United States Patent
Oki et al.

(10) Patent No.: US 12,281,347 B2
(45) Date of Patent: Apr. 22, 2025

(54) METHOD FOR PRODUCING 3-HYDROXYISOBUTYRIC ACID ESTER AND METHACRYLIC ESTER

(71) Applicants: Mitsubishi Chemical Corporation, Tokyo (JP); Toyama Prefectural University, Toyama (JP)

(72) Inventors: Kenji Oki, Tokyo (JP); Fujio Yu, Tokyo (JP); Kozo Murao, Tokyo (JP); Yasuhisa Asano, Toyama (JP); Fumihiro Motojima, Toyama (JP)

(73) Assignees: Mitsubishi Chemical Corporation, Tokyo (JP); Toyama Prefectural University, Toyama (JP)

( * ) Notice: Subject to any disclaimer, the term of this patent is extended or adjusted under 35 U.S.C. 154(b) by 0 days.

(21) Appl. No.: 17/006,976

(22) Filed: Aug. 31, 2020

(65) Prior Publication Data

US 2020/0392546 A1    Dec. 17, 2020

Related U.S. Application Data

(63) Continuation of application No. PCT/JP2019/008098, filed on Mar. 1, 2019.

(30) Foreign Application Priority Data

Mar. 2, 2018  (JP) ................................. 2018-037048

(51) Int. Cl.
*C12P 7/62*   (2022.01)
*C12N 1/21*   (2006.01)
*C12N 9/10*   (2006.01)

(52) U.S. Cl.
CPC .............. *C12P 7/62* (2013.01); *C12N 9/1029* (2013.01); *C12Y 203/01084* (2013.01)

(58) Field of Classification Search
None
See application file for complete search history.

(56) References Cited

U.S. PATENT DOCUMENTS

| 2013/0065279 | A1* | 3/2013 | Burk .......................... C12P 7/42 435/88 |
| 2014/0030779 | A1 | 1/2014 | Pharkya et al. |
| 2015/0184207 | A1 | 7/2015 | Sato et al. |
| 2016/0145665 | A1* | 5/2016 | Sato .......................... C12P 19/32 435/92 |
| 2017/0022525 | A1* | 1/2017 | Asano ........................ C12P 7/62 |
| 2019/0185825 | A1 | 6/2019 | Yu et al. |

FOREIGN PATENT DOCUMENTS

| AU | 2016340470 | B2 * | 10/2019 | ............. C12N 15/52 |
| CN | 103930558 | A | 7/2014 | |
| CN | 104619851 | A | 5/2015 | |
| CN | 104685058 | A | 6/2015 | |
| EP | 2090662 | A2 | 8/2009 | |
| EP | 2090662 | A3 | 10/2012 | |
| JP | H07-017909 | A | 1/1995 | |
| JP | 2015116141 | A | * 6/2015 | |
| WO | 2014/038214 | A1 | 3/2014 | |
| WO | 2015/133146 | A1 | 9/2015 | |
| WO | WO-2017069267 | A1 * | 4/2017 | ............. C12P 7/62 |
| WO | 2018/043546 | A1 | 3/2018 | |

OTHER PUBLICATIONS

Guterman et al., Generation of phenylpropanoid pathway-derived volatiles in transgenic plants, Plant Mol. Biol. 60, 2006, 555-63. (Year: 2006).*
Souleyre et al., An alcohol acyl transferase from apple (cv. Royal Gala), MpAAT1, produces esters involved in apple fruit flavor, FEBS J., 2005, 272:,3132-44. (Year: 2005).*
Hawes et al., Synthesis of methacrylyl-CoA and (R)- and (S)-3-hydroxyisobutyryl-CoA, Methods Enz. 324, 2000, 73-79. (Year: 2000).*
Teh et al., The draft genome of tropical fruit durian (*Durio zibethinus*), Nature Genetics 49, 2017, 1633-41. (Year: 2017).*
Genbank, Accession No. XP_022742021.1, 2017, www.ncbi.nlm.nih.gov. (Year: 2017).*
Goldberg, Protein degradation and protection against misfolded or damaged proteins, Nature 436, 2003, 895-99. (Year: 2003).*
International Search Report issued in related International Patent Application No. PCT/JJP2019/008098 dated May 28, 2019.
Oshima et al., "Purification and elucidation of enzymatic properties of an alcohol acyl transferase derived from Chamaemelum nobile and Durio zibethinus," Lecture Abstracts of the 70th Annual Meeting of the Society for Biotechnology 123 (2018).
Extended European Search Report issued in related European Patent Application No. 19761439.9 dated Apr. 1, 2021.
Database GenPept, "benzyl alcohol O-benzoyltranferase-like isoform X1," Accession No. XP_022742021.1 dated Oct. 25, 2017.
Office Action issued in corresponding Indonesian Patent Application No. P00202006813 dated Aug. 9, 2022.
Office Action issued in related Japanese Patent Application No. 2020-503642 dated Sep. 20, 2022.
Office Action issued in related Japanese Patent Application No. 2020-503642 dated Feb. 14, 2023.
Office Action issued in related Chinese Patent Application No. 201980016744.3 dated Mar. 22, 2023.
Office Action issued in Indian Patent Application No. 202047036646 dated May 17, 2023.
Hearing Notice issued Jul. 4, 2024 for Indian Patent Application No. 202047036646.

(Continued)

*Primary Examiner* — Todd M Epstein
(74) *Attorney, Agent, or Firm* — Morgan, Lewis & Bockius LLP

(57) ABSTRACT

As a method for producing a 3-hydroxyisobutyric acid ester using a biocatalyst, a method for producing a 3-hydroxyisobutyric acid ester, including a step of allowing an alcohol or phenol to act on 3-hydroxyisobutyryl-CoA in the presence of alcohol acyltransferase to produce a 3-hydroxyisobutyric acid ester is provided.

9 Claims, No Drawings

Specification includes a Sequence Listing.

(56) References Cited

OTHER PUBLICATIONS

Office Action issued May 23, 2024 for European Patent Application No. 19761439.9.
Office Action issued in corresponding Chinese Patent Application No. 201980016744.3 dated Oct. 18, 2023.

\* cited by examiner

```
                              SEQUENCE LISTING

<160> NUMBER OF SEQ ID NOS: 9

<210> SEQ ID NO 1
<211> LENGTH: 457
<212> TYPE: PRT
<213> ORGANISM: Durio zibethinus

<400> SEQUENCE: 1

Met Ala Gln Leu Pro Thr Ser Leu Val Phe Thr Ile Arg Arg Ser Glu
1               5                   10                  15

Ala Glu Leu Val Ala Pro Ala Lys Ala Thr Pro Arg Glu Tyr Lys Leu
                20                  25                  30

Leu Ser Asp Ile Asp Asp Gln Gln Ser Leu Arg Phe Gln Ile Pro Val
            35                  40                  45

Ile Gln Phe Tyr Arg Cys Asn Pro Cys Met Gln Gly Lys Asp Pro Ala
    50                  55                  60

Arg Val Ile Lys Asp Ala Leu Ala Gln Thr Leu Val Phe Tyr Tyr Pro
65                  70                  75                  80

Leu Ala Gly Arg Leu Arg Glu Gly Arg Asn Arg Lys Leu Ala Val Asp
                85                  90                  95

Cys Thr Gly Glu Gly Ala Leu Phe Ile Glu Ala Glu Ala Asp Val Lys
            100                 105                 110

Leu Glu Gln Phe Gly Asp Ala Leu Gln Pro Pro Phe Pro Cys Phe Asp
        115                 120                 125

Glu Leu Leu Tyr Asn Val Pro Gly Ser Glu Gly Met Leu Asn Cys Pro
130                 135                 140

Leu Leu Leu Ile Gln Val Thr Arg Leu Lys Cys Gly Gly Phe Ile Phe
145                 150                 155                 160

Ala Ile Arg Leu Asn His Val Leu Ala Asp Gly Ala Gly Met Ile Gln
                165                 170                 175

Phe Met Ser Ala Met Ala Glu Met Ser Arg Gly Ala Ile Ala Pro Ser
            180                 185                 190

Ile Pro Pro Lys Trp Glu Arg His Leu Leu Asp Ala Arg Asp Pro Pro
        195                 200                 205

Arg Ile Ser Phe Thr His Arg Glu Tyr Asp Glu Val Glu Gly Thr Ile
210                 215                 220

Ile Leu Ser Glu Asn Met Val Gln Arg Ser Phe Phe Phe Gly Pro Lys
225                 230                 235                 240

Glu Val Ser Thr Leu Arg Lys Leu Leu Pro His His Leu Arg Lys Cys
                245                 250                 255

Ser Lys Phe Asp Ile Leu Ala Ser Cys Leu Trp Arg Cys Arg Thr Ile
            260                 265                 270

Ala Ile Lys Pro Asp Pro Asp Glu Glu Val Arg Leu Leu Cys Val Val
        275                 280                 285

Asn Val Arg Ser Lys Leu Asn Pro Pro Ser Pro Ser Gly Phe Tyr Gly
290                 295                 300

Asn Ala Ile Val Phe Ser Ala Ala Ile Thr Thr Ala Arg Lys Leu Cys
305                 310                 315                 320

Gln Asn Pro Leu Gly Tyr Ala Val Glu Leu Val Lys Gln Ala Lys Glu
```

|     |     |     |     |     | 325 |     |     |     |     | 330 |     |     |     |     | 335 |     |
| --- | --- | --- | --- | --- | --- | --- | --- | --- | --- | --- | --- | --- | --- | --- | --- | --- |

Ser Val Thr Glu Glu Tyr Val Lys Ser Ala Ala Asp Phe Met Val Ile
            340                    345                    350

Lys Gly Lys Arg Leu His Tyr Thr Met Val Arg Ser Cys Val Ile Ser
            355                    360                    365

Asp Val Thr Arg Val Ala Phe Val Asp Val Asp Phe Gly Trp Gly Lys
    370                    375                    380

Ala Val Tyr Gly Gly Leu Ala Lys Ala Gly Ile Gly Ala Ile Pro Gly
385                    390                    395                    400

Ala Leu Ser Phe Leu Val Ala Ser Lys Asn Lys Asn Gly Glu Ala Gly
            405                    410                    415

Thr Leu Met Leu Ile Cys Leu Thr Ala Pro Ala Met Glu Arg Phe Ser
                420                    425                    430

Lys Glu Leu Asp Asn Met Ser Lys Glu Gln Pro Ala Asp Glu Met Gly
            435                    440                    445

Lys Ser Val Ser Ile Ser Ser Thr Leu
    450                    455

<210> SEQ ID NO 2
<211> LENGTH: 1374
<212> TYPE: DNA
<213> ORGANISM: Durio zibethinus

<400> SEQUENCE: 2

```
atggcacaac tgccaacttc cctagtattt acaattcgaa gaagcgaagc cgagcttgtt      60
gctccggcca aggccacacc tcgcgagtat aaactattat ccgacattga tgatcaacag     120
agtctccggt tccagattcc tgtcattcaa ttttatcggt gcaatccatg catgcaaggg     180
aaggaccctg caagggttat taaggatgca cttgcacaaa ccttagtttt ttattatcca     240
ttagctggta ggctaaggga aggtcgtaat cgcaagcttg cggtggattg caccggcgag     300
ggtgccttgt ttattgaggc tgaagctgat gttaaactcg agcaatttgg cgatgcactt     360
caaccgccat tcccttgctt tgatgagctc ctttacaatg ttccgggctc agaagggatg     420
ttgaattgcc ccttgctatt aattcaggta acaagactga aatgtggagg tttcatcttt     480
gccattcgcc tcaaccatgt cttagccgat ggtgctggca tgattcaatt catgtctgcc     540
atggctgaga tgagtcgtgg tgcaattgct ccctcaatcc cacccaagtg ggagaggcac     600
ctcttagatg ctcgtgatcc accacgaatc tcattcacgc accgtgagta cgatgaagta     660
gaaggcacta tcatcctatc ggaaaacatg gttcaacgct cctttttctt tggccccaaa     720
gaagtttcaa ctcttcgcaa gctgctaccg caccaccttc gtaagtgttc gaaatttgac     780
atcttagcat cgtgttttatg gcgttgtcga accattgcta taaaacctga ccctgatgaa     840
gaggtgcgat tgctatgcgt tgtcaatgta cgttccaagt tgaatcctcc atcaccgtca     900
ggatttatg ggaatgcaat tgtgttctca gcggcaataa caacagctag aaaactctgc     960
cagaatccgc taggatatgc agtggaacta gtgaagcaag caaggagag tgtgaccgaa    1020
gaatacgtta aatcagcagc agatttcatg gtgattaaag gtaaaagact ccactataca    1080
atggtgagat cttgtgttat atcagatgta acccgtgttg catttgtaga cgttgatttt    1140
gggtggggta aggcagttta tggtgggttg gccaaagctg gataggtgc tatacctggg    1200
gcattaagct ttcttgtagc atccaagaat aaaaatggag aggctggaac tcttatgcta    1260
atttgtttga cagctccagc tatggaaaga ttttccaagg aattggataa catgtcgaag    1320
gagcagccag ctgatgaaat gggtaaatca gtttctattt catctacttt gtaa          1374
```

<210> SEQ ID NO 3
<211> LENGTH: 455
<212> TYPE: PRT
<213> ORGANISM: Malus domestica

<400> SEQUENCE: 3

```
Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Ile Met Cys
        35                  40                  45

Tyr Lys Asp Asn Pro Ser Leu Asn Lys Asn Arg Asn Pro Val Lys Ala
50                  55                  60

Ile Arg Glu Ala Leu Ser Arg Ala Leu Val Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Lys Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
130                 135                 140

Leu Ile Gln Val Thr Cys Leu Thr Cys Gly Gly Phe Ile Leu Ala Leu
145                 150                 155                 160

Arg Leu Asn His Thr Met Cys Asp Ala Ala Gly Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
210                 215                 220

Ser Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
            260                 265                 270

Lys Cys Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Gln Tyr Ser Ser Thr Gly
        355                 360                 365

Ser Tyr Leu Ile Val Ser Asp Asn Thr Arg Val Gly Phe Gly Asp Val
```

```
                370               375               380
Asn Phe Gly Trp Gly Gln Pro Val Phe Ala Gly Pro Val Lys Ala Leu
385               390               395               400

Asp Leu Ile Ser Phe Tyr Val Gln His Lys Asn Asn Thr Glu Asp Gly
                405               410               415

Ile Leu Val Pro Met Cys Leu Pro Ser Ser Ala Met Glu Arg Phe Gln
                420               425               430

Gln Glu Leu Glu Arg Ile Thr Gln Glu Pro Lys Glu Asp Ile Cys Asn
                435               440               445

Asn Leu Arg Ser Thr Ser Gln
    450               455

<210> SEQ ID NO 4
<211> LENGTH: 1368
<212> TYPE: DNA
<213> ORGANISM: Artificial Sequence
<220> FEATURE:
<223> OTHER INFORMATION: Nucleic acid sequence of apple AAT gene with
      optimal codons

<400> SEQUENCE: 4
atgaaaagct tttctgtact ccaagtcaaa cgcctgcaac cagaactgat tacgccagcg      60
aaatcgaccc cgcaggaaac caaattcctg tctgacatcg atgaccaaga gagcttgcgt     120
gtgcagattc cgatcatcat gtgctataaa gacaaccccga gcctgaataa aatcgcaat    180 ccggttaagg ccattcgtga ggccctgtcc cgtgcgctgg tttactatta cccgctggcg     240
ggtcgtctgc gtgagggtcc gaatcgcaaa ctggtggtgg actgcaatgg tgagggtatt     300
ctgtttgttg aggcgagcgc ggacgtcacc ctggaacagc tgggcgacaa gatcctgccg     360
ccgtgtccgc tgttggaaga gtttctgtac aacttcccgg cagcgatgg tatcatcgat     420 tgcccgctgc tgctgattca agtcacttgt ctgacgtgtg gtggctttat tctggctctg    480
cgcctgaacc acaccatgtg tgatgcagcg ggtttgttgc tgttcctgac cgccatcgca    540
gagatggccc gtggtgccca cgcaccgagc attctgccgg tgtgggaacg tgaactgctg    600
ttcgcacgtg acccgcctcg tattacttgc gcgcaccatg aatacgagga cgttatcggc    660
catagcgacg gcagctacgc gagcagcaac caaagcaata tggtgcagcg tagcttttac    720
ttcggcgcga agaaaatgcg tgttctgcgc aagcagatcc cgcctcacct gatcagcacg    780
tgcagcacct tgatttgat taccgcatgc ctgtggaagt gccgtacgct ggcgctgaac    840
atcaacccga agaagccgt ccgtgtgagc tgtatcgtta cgcgcgtgg taaacacaac    900 aatgttcgcc tgccgctggg ctattacggc aatgcgttcg cattcccggc tgctatctct    960
aaggcagagc cgctgtgtaa gaaccctctg ggttacgccc tggagttggt gaagaaggcg   1020
aaagcgacca tgaatgaaga gtatctgcgc agcgtggcgg atctgctggt tttgcgcggt   1080
cgtccgcaat actccagcac gggttcctat ctgattgtga gcgacaatac ccgcgtgggt   1140
tttggtgatg tcaacttcgg ttggggccag ccagtctttg ctggcccggt caaagcattg   1200
gacctgatta gcttctatgt tcaacataag aacaacacgg aagatggtat cttggttccg   1260
atgtgcctgc cgtcctcggc gatggagcgt ttccaacagg agctggagcg cattacccag   1320
gaaccgaaag aggatatttg caacaatctg cgtagcacca gccagtaa              1368

<210> SEQ ID NO 5
<211> LENGTH: 442
<212> TYPE: PRT
<213> ORGANISM: Artificial Sequence
```

```
<220> FEATURE:
<223> OTHER INFORMATION: Amino acid sequence of tomato A2K AAT

<400> SEQUENCE: 5

Met Lys Asn Thr Leu Pro Ile Ser Ile Asn Tyr His Lys Pro Lys Leu
1               5                   10                  15

Val Val Pro Ser Ser Val Thr Pro His Glu Thr Lys Arg Leu Ser Glu
                20                  25                  30

Ile Asp Asp Gln Gly Phe Ile Arg Phe Gln Ile Pro Ile Leu Met Phe
            35                  40                  45

Tyr Lys Tyr Asn Ser Ser Met Lys Gly Lys Asp Pro Ala Arg Ile Ile
        50                  55                  60

Glu Asp Gly Leu Ser Lys Thr Leu Val Phe Tyr His Pro Leu Ala Gly
65                  70                  75                  80

Arg Leu Ile Glu Gly Pro Asn Lys Lys Leu Met Val Asn Cys Asn Gly
                85                  90                  95

Glu Gly Val Leu Phe Ile Glu Gly Asp Ala Asn Ile Glu Leu Glu Lys
            100                 105                 110

Leu Gly Glu Ser Ile Lys Pro Pro Cys Pro Tyr Leu Asp Leu Leu Leu
        115                 120                 125

His Asn Val Pro Gly Ser Asp Gly Ile Ile Gly Ser Pro Leu Leu Leu
    130                 135                 140

Ile Gln Val Thr Arg Phe Thr Cys Gly Gly Phe Ala Val Gly Phe Arg
145                 150                 155                 160

Val Ser His Thr Met Met Asp Gly Tyr Gly Phe Lys Met Phe Leu Asn
                165                 170                 175

Ala Leu Ser Glu Leu Ile Gln Gly Ala Ser Thr Pro Ser Ile Leu Pro
            180                 185                 190

Val Trp Gln Arg His Leu Leu Ser Ala Arg Ser Ser Pro Cys Ile Thr
        195                 200                 205

Cys Ser His His Glu Phe Asp Glu Gly Ile Glu Ser Lys Ile Ala Trp
    210                 215                 220

Glu Ser Met Glu Asp Lys Leu Ile Gln Glu Ser Phe Phe Gly Asn
225                 230                 235                 240

Glu Glu Met Glu Val Ile Lys Asn Gln Ile Pro Pro Asn Tyr Gly Cys
                245                 250                 255

Thr Lys Phe Glu Leu Leu Met Ala Phe Leu Trp Lys Cys Arg Thr Ile
            260                 265                 270

Ala Leu Asp Leu His Pro Glu Glu Ile Val Arg Leu Thr Tyr Val Ile
        275                 280                 285

Asn Ile Arg Gly Lys Lys Ser Leu Asn Ile Glu Leu Pro Ile Gly Tyr
    290                 295                 300

Tyr Gly Asn Ala Phe Val Thr Pro Val Val Ser Lys Ala Gly Leu
305                 310                 315                 320

Leu Cys Ser Asn Pro Val Thr Tyr Ala Val Glu Leu Ile Lys Lys Val
                325                 330                 335

Lys Asp His Ile Asn Glu Glu Tyr Ile Lys Ser Val Ile Asp Leu Thr
            340                 345                 350

Val Ile Lys Gly Arg Pro Glu Leu Thr Lys Ser Trp Asn Phe Leu Val
        355                 360                 365

Ser Asp Asn Arg Tyr Ile Gly Phe Asp Glu Phe Asp Phe Gly Trp Gly
    370                 375                 380

Asn Pro Ile Phe Gly Gly Ile Ser Lys Ala Thr Ser Phe Ile Ser Phe
385                 390                 395                 400
```

Gly Val Ser Val Lys Asn Asp Lys Gly Glu Lys Gly Val Leu Ile Ala
            405                 410                 415

Ile Ser Leu Pro Pro Leu Ala Met Lys Lys Leu Gln Asp Ile Tyr Asn
            420                 425                 430

Met Thr Phe Arg Val Ile Ile Pro Arg Ile
            435                 440

<210> SEQ ID NO 6
<211> LENGTH: 1329
<212> TYPE: DNA
<213> ORGANISM: Artificial Sequence
<220> FEATURE:
<223> OTHER INFORMATION: Nucleic acid sequence of tomato A2K AAT gene
      with optimal codons

<400> SEQUENCE: 6

```
atgaagaata ccctgccgat tagcatcaac tatcacaagc cgaaactggt ggttccgagc      60
agcgttaccc cgcacgagac caagcgtctg agcgagatcg acgatcaggg ttttattcgt     120
ttccaaatcc cgatcctgat gttctacaag tacaacagca gcatgaaggg caaagacccg     180
gcgcgtatca ttgaggatgg tctgagcaag accctggttt ctaccaccc gctggcgggc      240
cgtctgattg aaggtccgaa caagaaactg atggttaact gcaacggcga gggcgtgctg     300
tttatcgaag cgacgcgaa cattgagctg gaaaaactgg cgagagcat caagccgccg      360
tgcccgtacc tggacctgct gctgcacaac gttccgggta gcgatggcat cattggtagc     420
ccgctgctgc tgatccaggt gacccgtttc acctgcggtg gctttgcggt tggcttccgt     480
gtgagccaca ccatgatgga tggttatggc tttaaaatgt tcctgaacgc gctgagcgaa     540
ctgatccagg gtgcgagcac cccgagcatt ctgccggttt ggcaacgtca cctgctgagc     600
gcgcgtagca gcccgtgcat cacctgtagc caccacgagt tcgacgagga aatcgaaagc     660
aaaattgcgt gggagagcat ggaagataag ctgattcagg agagcttctt tttcggcaac     720
gaggaaatgg aagtgatcaa aaaccaaatt ccgccgaatt acggttgcac caaatttgag     780
ctgctgatgg cgttcctgtg gaagtgccgt accattgcgc tggacctgca cccggaggaa     840
attgttcgtc tgacctatgt gatcaacatt cgtggcaaga aaagcctgaa catcgagctg     900
ccgattggct actatggtaa cgcgtttgtt accccggtgg ttgtgagcaa ggcgggtctg     960
ctgtgcagca cccggttac ctacgcggtg gaactgatca agaaagtgaa agaccacatt    1020
aacgaggaat atatcaagag cgttattgat ctgaccgtga tcaaaggccg tccggagctg    1080
accaagagct ggaactttct ggttagcgac aaccgttata ttggtttcga cgaatttgat    1140
ttcggttggg caacccgat cttcggtggc attagcaagg cgaccagctt tatcagcttc    1200
ggtgttagcg tgaagaacga taaaggcgaa aagggtgtgc tgatcgcgat tagcctgccg    1260
ccgctggcga tgaaaaaact gcaagacatt tacaacatga ccttccgtgt gattatcccg    1320
cgtatctaa                                                          1329
```

<210> SEQ ID NO 7
<211> LENGTH: 455
<212> TYPE: PRT
<213> ORGANISM: Artificial Sequence
<220> FEATURE:
<223> OTHER INFORMATION: Amino acid sequence of mutated apple AAT

<400> SEQUENCE: 7

Met Lys Ser Phe Ser Val Leu Gln Val Lys Arg Leu Gln Pro Glu Leu
1               5                   10                  15

```
Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Met Ala
        35                  40                  45

Tyr Lys Asp Asn Pro Ser Leu Asn Lys Asn Arg Asn Pro Val Lys Val
    50                  55                  60

Ile Arg Glu Ala Leu Ser Arg Ala Leu Val Tyr Tyr Pro Leu Ala
65                  70                  75                  80

Gly Arg Leu Arg Glu Gly Pro Asn Arg Lys Leu Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
    130                 135                 140

Leu Ile Gln Val Thr Arg Leu Thr Cys Gly Gly Phe Ile Leu Ala Leu
145                 150                 155                 160

Arg Leu Asn His Thr Met Ala Asp Ala Ala Gly Leu Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Ala Leu Trp
            260                 265                 270

Lys Ala Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
        355                 360                 365

Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430
```

Gln Glu Leu Glu Arg Ile Thr Gln Glu Pro Lys Glu Asp Ile Ala Asn
        435                 440                 445

Asn Leu Arg Ser Thr Ser Gln
        450                 455

<210> SEQ ID NO 8
<211> LENGTH: 1368
<212> TYPE: DNA
<213> ORGANISM: Artificial Sequence
<220> FEATURE:
<223> OTHER INFORMATION: Nucleic acid sequence of mutated apple AAT gene
      with optimal codons

<400> SEQUENCE: 8

| | | |
|---|---|---|
| atgaaaagct tttctgtact ccaagtcaaa cgcctgcaac cagaactgat tacgccagcg | 60 |
| aaatcgaccc cgcaggaaac caaattcctg tctgacatcg atgaccaaga gagcttgcgt | 120 |
| gtgcagattc cgatcatcat ggcgtataaa gacaacccga gcctgaataa gaatcgcaat | 180 |
| ccggttaagg tgattcgtga ggccctgtcc cgtgcgctgg tttactatta cccgctggcg | 240 |
| ggtcgtctgc gtgagggtcc gaatcgcaaa ctggtggtgg actgcaatgg tgagggtatt | 300 |
| ctgtttgttg aggcgagcgc ggacgtcacc ctggaacagc tgggcgacca gatcctgccg | 360 |
| ccgtgtccgc tgttggaaga gtttctgtac aacttcccgg gcagcgatgg tatcatcgat | 420 |
| tgcccgctgc tgctgattca agtcactcgt ctgacgtgtg gtggctttat tctggctctg | 480 |
| cgcctgaacc acaccatggc ggatgcagcg ggtttgttgc tgttcctgac cgccatcgca | 540 |
| gagatggccc gtggtgccca cgcaccgagc attctgccgg tgtgggaacg tgaactgctg | 600 |
| ttcgcacgtg acccgcctcg tattacttgc gcgcaccatg aatacgagga cgttatcggc | 660 |
| catagcgacg gcagctacgc gagcagcaac caaagcaata tggtgcagcg tagcttttac | 720 |
| ttcggcgcga agaaatgcg tgcgctgcgc aagcagatcc cgcctcacct gatcagcacg | 780 |
| tgcagcacct ttgatttgat taccgcagcg ctgtggaagg cccgtacgct ggcgctgaac | 840 |
| atcaacccga agaagccgt ccgtgtgagc tgtatcgtta acgcgcgtgg taaacacaac | 900 |
| aatgttcgcc tgccgctggg ctattacggc aatgcgttcg cattcccggc tgctatctct | 960 |
| aaggcagagc cgctgtgtaa gaaccctctg ggttacgccc tggagttggt gaagaaggcg | 1020 |
| aaagcgacca tgaatgaaga gtatctgcgc agcgtggcgg atctgctggt tttgcgcggt | 1080 |
| cgtccgaaat actccagcac gggttcctat ctgattgtga cgacaatac ccgcgtgggt | 1140 |
| tttggtgatg tcaacttcgg ttggggccag ccagtctttg ctggcccggt caaagcattg | 1200 |
| gacctgatta gcttctatgt tcaacataag aacaacacgg aagatggtat cttggttccg | 1260 |
| atgtgcctgc gtcctcggc gatggagcgt ttccaacagg agctggagcg cattacccag | 1320 |
| gaaccgaaag aggatattgc gaacaatctg cgtagcacca gccagtaa | 1368 |

<210> SEQ ID NO 9
<211> LENGTH: 1404
<212> TYPE: DNA
<213> ORGANISM: Artificial Sequence
<220> FEATURE:
<223> OTHER INFORMATION: Nucleic acid sequnce of durian AAT gene with
      optimal codons

<400> SEQUENCE: 9

| | | |
|---|---|---|
| aacctgtatt ttcagggtgc acagctgccg accagcctgg ttttaccat tcgtcgtagc | 60 |
| gaagcagaac tggttgcacc ggcaaaagca acaccgcgtg aatataaact gctgagcgat | 120 |
| attgatgatc agcagagcct gcgttttcag attccggtta ttcagttta tcgttgcaat | 180 |

```
ccgtgtatgc agggtaaaga tccggcacgt gttattaaag atgcactggc acagaccctg    240
gttttctatt atccgctggc aggtcgtctg cgtgaaggtc gtaatcgtaa actggcagtt    300
gattgtaccg gtgaaggtgc actgtttatt gaagccgaag cagatgttaa actggaacag    360
tttggtgatg ccctgcagcc tccgtttccg tgttttgatg aactgctgta taatgttccg    420
ggtagcgaag gtatgctgaa ttgtccgctg ctgctgattc aggttacccg tctgaaatgt    480
ggtggtttta tctttgccat tcgtctgaat catgttctgg cagatggtgc aggtatgatt    540
cagtttatga gcgcaatggc agaaatgagc cgtggtgcca ttgcaccgag cattccgcct    600
aaatgggaac gtcatctgct ggatgcacgt gatccgcctc gtattagctt tacccatcgt    660
gaatatgatg aagtggaagg caccattatt ctgagcgaaa atatggttca gcgcagcttt    720
tttttcggtc cgaaagaagt tagcaccctg cgcaaactgc tgccgcatca tctgcgtaaa    780
tgtagcaaat ttgatattct ggcaagctgt ctgtggcgtt gtcgtaccat tgcaattaaa    840
ccggatcctg atgaagaggt tcgtctgctg tgtgttgtta atgttcgtag caaactgaac    900
cctccgagcc cgagcggttt ttatggtaat gcaattgttt ttagcgcagc cattaccacc    960
gcacgtaaac tgtgtcagaa tccgctgggt tatgcagttg aactggttaa acaggccaaa   1020
gaaagcgtta ccgaagaata tgttaaaagc gcagccgatt tcatggtgat taaaggtaaa   1080
cgtctgcact ataccatggt tcgtagctgt gttattagtg atgttacccg tgttgccttt   1140
gtggatgttg attttggttg gggtaaagcc gtttatggtg gtctggcaaa agccggtatt   1200
ggtgcaattc cgggtgcact gagctttctg gttgcaagca aaacaaaaa tggtgaagca   1260
ggcaccctga tgctgatttg tctgaccgct ccggcaatgg aacgttttag caaagaactg   1320
gataacatgt ccaaagaaca gcctgcagat gaaatgggta aaagcgttag cattagcagc   1380
accctgtaag gatccgaatt cgag                                           1404
```

METHOD FOR PRODUCING 3-HYDROXYISOBUTYRIC ACID ESTER AND METHACRYLIC ESTER

TECHNICAL FIELD

The present invention relates to a method for producing a 3-hydroxyisobutyric acid ester and a methacrylic ester. More specifically, the present invention relates to a method for producing a 3-hydroxyisobutyric acid ester from 3-hydroxyisobutyryl-CoA using a catalytic reaction of alcohol acyltransferase.

BACKGROUND ART

Methacrylic esters are mainly used as a starting material for acrylic resins and often demanded as co-monomers in the fields such as paints, adhesives and resin modifiers. A methacrylic ester is produced by dehydrating, for example, a 3-hydroxyisobutyric acid ester using a chemical approach.

Alcohol acyltransferase is known as an enzyme for synthesizing fruity flavors. Patent Literatures 1 and 2 disclose reactions in which an alcohol or phenol is allowed to act on methacrylyl-CoA in the presence of alcohol acyltransferase to produce a methacrylic ester. In these reactions, a CoA compound constituted of a chain hydrocarbon is used as a starting material.

If a hydroxyl group is introduced into the chain hydrocarbon of a CoA compound, the physicochemical properties of the CoA compound may change; however, it has not yet been known whether the esterification reaction of the CoA compound composed of the chain hydrocarbon and hydroxylated can be catalyzed by alcohol acyltransferase.

CITATION LIST

Patent Literature

Patent Literature 1: International Publication No. WO 2014/038214
Patent Literature 2: International Publication No. WO 2015/133146
Patent Literature 3: Japanese Patent Laid-Open No. 7-17909

SUMMARY OF INVENTION

Technical Problem

A primary object of the present invention is to provide a method for producing a 3-hydroxyisobutyric acid ester using a biocatalyst.

Solution to Problem

To attain the above object, the present invention will provide the following [1] to [19].

[1] A method for producing a 3-hydroxyisobutyric acid ester, comprising a step of allowing an alcohol or phenol to act on 3-hydroxyisobutyryl-CoA in the presence of alcohol acyltransferase.
[2] The method for producing a 3-hydroxyisobutyric acid ester according to [1], wherein the alcohol acyltransferase is derived from a plant.
[3] The method for producing a 3-hydroxyisobutyric acid ester according to [2], wherein the plant belongs to Malvales, Rosales or Solanales.
[4] The method for producing a 3-hydroxyisobutyric acid ester according to [2], wherein the plant belongs to Malvaceae, Rosaceae or Solanaceae.
[5] The method for producing a 3-hydroxyisobutyric acid ester according to [2], wherein the plant belongs to *Durio, Malus* or *Solanum*.
[6] The method for producing a 3-hydroxyisobutyric acid ester according to [2], wherein the plant is durian, apple or tomato.
[7] The method for producing a 3-hydroxyisobutyric acid ester according to any one of [1] to [6], wherein the alcohol acyltransferase comprises any one of the following amino acid sequences (1) to (4):
(1) an amino acid sequence represented by SEQ ID NO:1, SEQ ID NO:5 or SEQ ID NO:7;
(2) an amino acid sequence derived from the amino acid sequence represented by SEQ ID NO:1, SEQ ID NO:5 or SEQ ID NO:7 by deletion, insertion, substitution and/or addition of one or several amino acids;
(3) an amino acid sequence having a sequence identity of 80% or more with the amino acid sequence represented by SEQ ID NO:1, SEQ ID NO:5 or SEQ ID NO:7; and
(4) an amino acid sequence encoded by DNA that hybridizes with a complementary strand of the nucleotide sequence represented by SEQ ID NO:2, SEQ ID NO:6 or SEQ ID NO:8 under stringent conditions.
[8] The method for producing a 3-hydroxyisobutyric acid ester according to any one of [1] to [7], wherein a genetically modified microorganism expressing the alcohol acyltransferase is used.
[9] The method for producing a 3-hydroxyisobutyric acid ester according to [8], wherein the 3-hydroxyisobutyryl-CoA is synthesized from methacrylyl-CoA in vivo within the microorganism.
[10] A method for producing a methacrylic ester, comprising the steps of:
allowing an alcohol or phenol to act on 3-hydroxyisobutyryl-CoA in the presence of alcohol acyltransferase to produce a 3-hydroxyisobutyric acid ester, and
subjecting the 3-hydroxyisobutyric acid ester to a dehydration reaction to produce a methacrylic ester.
[11] The method for producing a methacrylic ester according to [10], wherein the alcohol acyltransferase is derived from a plant.
[12] The method for producing a methacrylic ester according to [11], wherein the plant belongs to Malvales, Rosales or Solanales.
[13] The method for producing a methacrylic ester according to [11], wherein the plant belongs to Malvaceae, Rosaceae or solanaceae.
[14] The method for producing a methacrylic ester according to [11], wherein the plant belongs to *Durio, Malus* or *Solanum*.
[15] The method for producing a methacrylic ester according to [11], wherein the plant is durian, apple or tomato.
[16] The method for producing a methacrylic ester according to any one of [10] to [15], wherein the alcohol acyltransferase comprises any one of the following amino acid sequences (1) to (4):
(1) an amino acid sequence represented by SEQ ID NO:1, SEQ ID NO:5 or SEQ ID NO:7;
(2) an amino acid sequence derived from the amino acid sequence represented by SEQ ID NO:1, SEQ ID NO:5 or SEQ ID NO:7 by deletion, insertion, substitution and/or addition of one or several amino acids;

(3) an amino acid sequence having a sequence identity of 80% or more with the amino acid sequence represented by SEQ ID NO:1, SEQ ID NO:5 or SEQ ID NO:7; and (4) an amino acid sequence encoded by DNA that hybridizes with a complementary strand of a nucleotide sequence represented by SEQ ID NO:2, SEQ ID NO:6 or SEQ ID NO:8 under stringent conditions.

[17] The method for producing a methacrylic ester according to any one of [10] to [16], wherein a genetically modified microorganism expressing the alcohol acyltransferase is used.

[18] The method for producing a methacrylic ester according to [17], wherein the 3-hydroxyisobutyryl-CoA is synthesized from methacrylyl-CoA in vivo within the microorganism.

[19] A protein that is any one of the following proteins (1) to (4):

(1) a protein comprising an amino acid sequence represented by the SEQ ID NO:1;

(2) a protein comprising an amino acid sequence derived from the amino acid sequence represented by the SEQ ID NO:1 by deletion, insertion, substitution and/or addition of one or several amino acids, and having an alcohol acyltransferase activity that catalyzes esterification of 3-hydroxyisobutyryl-CoA;

(3) a protein comprising the amino acid sequence represented by the SEQ ID NO:1 or an amino acid sequence having a sequence identity of 80% or more with the amino acid sequence represented by the SEQ ID NO:1 and having an alcohol acyltransferase activity that catalyzes esterification of 3-hydroxyisobutyryl-CoA; and (4) a protein comprising an amino acid sequence encoded by DNA that hybridizes with the nucleotide sequence represented by SEQ ID NO:2 or a complementary strand of the nucleotide sequence represented by SEQ ID NO:2 under stringent conditions, and having an alcohol acyltransferase activity that catalyzes esterification of 3-hydroxyisobutyryl-CoA.

Advantageous Effect of Invention

According to the present invention, a method for producing a 3-hydroxyisobutyric acid ester using a biocatalyst is provided.

DESCRIPTION OF EMBODIMENTS

Hereinafter, a preferred embodiment for carrying out the present invention will be described. Note that a typical embodiment will be described below just as an example, which should not be construed as narrowing the scope of the present invention.

[Method for Producing a 3-Hydroxyisobutyric Acid Ester and a Methacrylic Ester]

A method for producing a 3-hydroxyisobutyric acid ester according to the present invention include the following "step A". A method for producing a methacrylic ester according to the present invention include the following "step B" in addition to step A.

Step A: allowing an alcohol or phenol to act on 3-hydroxyisobutyryl-CoA in the presence of alcohol acyltransferase to produce a 3-hydroxyisobutyric acid ester.

Step B: subjecting the 3-hydroxyisobutyric acid ester to a dehydration reaction to produce a methacrylic ester.

Step A and step B are shown below.

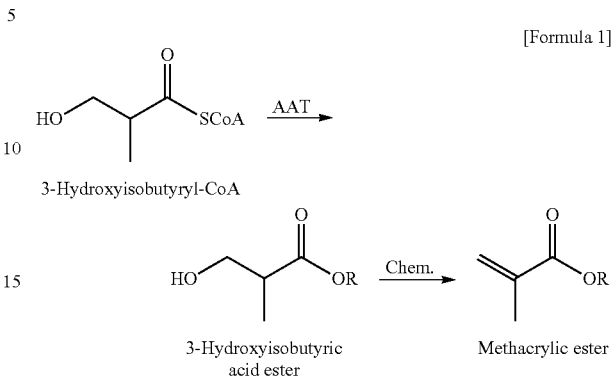

[Formula 1]

3-Hydroxyisobutyryl-CoA

3-Hydroxyisobutyric acid ester

Methacrylic ester

In the present invention, the "methacrylic ester" refers to a compound represented by Formula 1. In Formula 1, R represents a linear or branched hydrocarbon group having 1 to 20 carbon atoms. The hydrocarbon group may be a saturated or unsaturated acyclic group or a saturated or unsaturated cyclic group. Preferably, R represents a linear or branched unsubstituted alkyl group, aralkyl group or aryl group having 1 to 10 carbon atoms. Particularly preferably, R represents an alkyl group having 1 to 8 carbon atoms such as a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a n-hexyl group, an isohexyl group, a 2-hexyl group, a dimethylbutyl group, an ethylbutyl group, a heptyl group, an octyl group or a 2-ethylhexyl group; a benzyl group or a phenyl group.

$$CH_2=C(CH_3)COO-R \quad \text{(Formula 1)}$$

[Alcohol and Phenol]

The "alcohol" or "phenol" used in step A is a compound represented by Formula 2 below. Since the structure of an alcohol or phenol corresponds to that of a methacrylic ester, the structure is the same as defined as R in Formula 1 described above and represents a linear or branched hydrocarbon group having 1 to 20 carbon atoms. The hydrocarbon group may be a saturated or unsaturated acyclic group or a saturated or unsaturated cyclic group. The hydrocarbon group is preferably a linear or branched unsubstituted alcohol having 1 to 10 carbon atoms, an aralkyl alcohol or a phenol; more preferably an alkyl alcohol having 1 to 8 carbon atoms such as methanol, ethanol, n-propanol, isopropanol, n-butanol, isobutanol, sec-butanol, tert-butanol, n-pentyl alcohol, isopentyl alcohol, tert-pentyl alcohol, n-hexyl alcohol, isohexyl alcohol, 2-hexyl alcohol, dimethyl butyl alcohol, ethyl butyl alcohol, heptyl alcohol, octyl alcohol or 2-ethylhexyl alcohol; a benzyl alcohol or a phenol; and particularly preferably, methanol, ethanol, n-butanol, isobutanol and n-hexyl alcohol.

$$R-OH \quad \text{(Formula 2)}$$

[Alcohol Acyltransferase]

Alcohol acyltransferase (hereinafter referred to also as "AAT") has an activity to catalyze the reaction of transferring an acyl group of acyl-CoA to an alcohol or phenol to produce an ester. AAT is reported to be responsible for producing esters in various fruits. AAT is known to be present in plants such as Zingiberales (banana), Rosales (strawberry, apple, pear, peach), Cucurbitales (melon), Ericales (kiwi), Lamiales (olive), Solanales (tomato) and Sapindales (lemon, mango).

AAT used in step A has an activity to catalyze the reaction of transferring the acyl group of, particularly, 3-hydroxyisobutyryl-CoA, to an alcohol or phenol to produce a 3-hydroxyisobutyric acid ester (hereinafter referred to simply as "catalytic activity" or also as "AAT activity").

AAT used in step A is not limited in origin as long as it has the catalytic activity as mentioned above. AAT is preferably derived from a plant. AAT derived from a plant belonging to any one of the orders such as Zingiberales, Rosales, Ericales, Cucurbitales, Brassicales, Laurales, Poales, Arecales, Asparagales, Saxifragales, Caryophyllales, Vitales, Malpighiales, Oxalidales, Fabales, Sapindales, Malvales, Myrtales, Ranunculales, Solanales, Lamiales, Gentianales, Magnoliales and Asterales, can be suitably used. Of them, AAT derived from any one of the plants belonging to Malvales, Rosales and Solanales, is more preferable.

Note that, in the present invention, plants are classified in accordance with APG plant classification system, third edition (Botanical Journal of the Linnean Society, 2009, 161, 105121).

AAT can be easily obtained from any one of the plants mentioned above in accordance with the following method. First, an appropriate part of a plant tissue, if necessary, is cut into pieces. To the cut pieces, a solution containing 3-hydroxyisobutyryl-CoA and an alcohol or phenol is added. The mixture is shaken and allowed to react for a predetermined time. The presence or absence of a 3-hydroxyisobutyric acid ester in the reaction solution is checked by gas chromatography (GC) to confirm catalytic activity. To describe more specifically, for example, a leaf, a flower, a bud, pulp or pericarp is cut into pieces. To the pieces, a solution containing 0.01 to 10 mM 3-hydroxyisobutyryl-CoA and n-butanol (2 to 50 fold molar amount) is added. The mixture is shaken at 30° C. for 1 to 10 hours. After completion of the reaction, the presence or absence of butyl 3-hydroxyisobutyrate is checked by GC. In this manner, AAT available in the present invention can be obtained.

As a plant belonging to Zingiberales, Musaceae and Zingiberaceae are preferable;
as a plant belonging to Rosales, Rosaceae and Moraceae;
as a plant belonging to Ericales, Ericaceae, Actinidiaceae, Ebenaceae and Theaceae;
as a plant belonging to Cucurbitales, Cucurbitaceae;
as a plant belonging to Brassicales, Caricaceae and Brassicaceae;
as a plant belonging to Laurales, Lauraceae;
as a plant belonging to Poales, Bromeliaceae and Poaceae;
as a plant belonging to Arecales, Arecaceae;
as a plant belonging to Asparagales, Orchidaceae and Iridaceae;
as a plant belonging to Saxifragales, Grossulariaceae;
as a plant belonging to Caryophyllales, Caryophyllaceae;
as a plant belonging to Vitales, Vitaceae;
as a plant belonging to Malpighiales, Malpighiaceae, Passifloraceae, Euphorbiaceae and Salicaceae;
as a plant belonging to Oxalidales, Oxalidaceae;
as a plant belonging to Fabales, Fabaceae;
as a plant belonging to Sapindales, Anacardiaceae, Biebersteiniaceae, Burseraceae, Kirkiaceae, Meliaceae, Nitrariaceae, Rutaceae, Sapindaceae and Simaroubaceae;
as a plant belonging to Malvales, Bixaceae, Cistaceae, Cytinaceae, Dipterocarpaceae, Malvaceae, Muntingiaceae, Neuradaceae, Sarcolaenaceae, Sphaerosepalaceae and Thymelaeaceae;
as a plant belonging to Myrtales, Lythraceae, Onagraceae and Myrtaceae;
as a plant belonging to Ranunculales, Ranunculaceae and Papaveraceae;
as a plant belonging to Solanales, Solanaceae;
as a plant belonging to Lamiales, Acanthaceae, Bignoniaceae, Byblidaceae, Calceolariaceae, Carlemanniaceae, Gesneriaceae, Lamiaceae, Linderniaceae, Lentibulariaceae, Martyniaceae, Oleaceae, Orobanchaceae, Paulowniaceae, Pedaliaceae, Phrymaceae, Plantaginaceae, Plocospermataceae, Schlegeliaceae, Scrophulariaceae, Stilbaceae, Tetrachondraceae, Thomandersiaceae and Verbenaceae;
as a plant belonging to Gentianales, Apocynaceae;
as a plant belonging to Magnoliales, Annonaceae, Degeneriaceae, Eupomatiaceae, Himantandraceae, Magnoliaceae and Myristicacea; and as a plant belonging to *Chrysanthemum*, Alseuosmiaceae, Argophyllaceae, Asteraceae, Calyceraceae, Campanulaceae, Goodeniaceae, Menyanthaceae, Pentaphragmataceae, Phellinaceae, Rousseaceae and Stylidiaceae. Related species of the plants mentioned above can also be used.

Of them, a plant belonging to Malvaceae, Rosaceae or Solanaceae is more preferable.

As a plant belonging to Musaceae, *Musa* is preferable;
as a plant belonging to Zingiberaceae, *Zingiber;*
as a plant belonging to Rosaceae, *Fragaria, Malus, Prunus, Pyrus, Eriobotrya, Chaenomeles, Rubus* and *Rosa;*
as a plant belonging to Moraceae, *Ficus;*
as a plant belonging to Ericaceae, *Vaccinium;*
as a plant belonging to Actinidiaceae, *Actinidia;*
as a plant belonging to Ebenaceae, *Diospyros;*
as a plant belonging to Theaceae, *Camellia;*
as a plant belonging to Cucurbitaceae, *Cucumis* and *Citrullus;*
as a plant belonging to Caricaceae, *Carica* and *Vasconcellea;*
as a plant belonging to Brassicaceae, *Arabidopsis;*
as a plant belonging to Lauraceae, *Persea;*
as a plant belonging to Bromeliaceae, *Ananas;*
as a plant belonging to Poales, *Oryza, Triticum, Hordeum, Zea, Sorghum* and *Brachypodium;*
as a plant belonging to Arecaceae, *Cocos;*
as a plant belonging to Orchidaceae, *Vanda;*
as a plant belonging to Iridaceae, *Iris;*
as a plant belonging to Grossulariaceae, *Ribes;*
as a plant belonging to Caryophyllaceae, *Gypsophila;*
as a plant belonging to Vitales, *Vitis, Ampelopsis, Cayratia, Cissus, Cyphostemma, Leea, Parthenocissus* and *Tetrastigma;*
as a plant belonging to Malpighiales, *Malpighia*, as a plant belonging to Passifloraceae, *Passiflora;*
as a plant belonging to Euphorbiaceae, *Ricinus*, as a plant belonging to Salicaceae, *Populus;*
as a plant belonging to Oxalidaceae, *Averrhoa;*
as a plant belonging to Fabaless, *Medicago, Lupinus, Glycine* and *Clitoria;*
as a plant belonging to Anacardiaceae, *Mangifera;*
as a plant belonging to Rutaceae, *Citrus, Aegle, Zanthoxylum, Murraya, Ruta, Orixa, Skimmia, Euodia, Phellodendron, Boronia, Acronychia, Clausena, Correa, Glycosmis* and *Melicope;*
as a plant belonging to Sapindaceae, *Litchi;*
as a plant belonging to Malvaceae, *Durio, Theobroma, Abutilon, Abelmoschus, Gossypium, Pavonia, Hibiscus, Sida* and *Malva;* as a plant belonging to Lythraceae, *Punica,*
as a plant belonging to Onagraceae, *Clarkia;*
as a plant belonging to Myrtaceae, *Psidium;*
as a plant belonging to Ranunculaceae, *Actaea,*
as a plant belonging to Papaveraceae, *Papaver;*
as a plant belonging to Solanaceae, *Solanum, Capsicum, Nicotiana* and *Petunia;*
as a plant belonging to Oleaceae, *Osmanthus Olea, Jasminum, Forsythia, Syringa, Chionanthus, Fraxinus* and *Ligustrum;*
as a plant belonging to Lamiaceae, *Salvia;*
as a plant belonging to Verbenaceae, *Glandularia;*
as a plant belonging to Apocynaceae, *Rauvolfia* and *Catharanthus;*
as a plant belonging to Magnoliaceae, *Magnolia;*
as a plant belonging to Asteraceae, *Chamaemelum, Achillea, Echinacea, Matricaria, Tanacetum, Taraxacum, Artemisia, Petasites, Helichrysum, Santolina, Cynara, Silybum, Calendula, Cichorium, Carthamus* and *Chrysanthemum.*

Of these, a plant belonging to *Durio, Malus* or *Solanum* is more preferable.

As a plant belonging to *Musa, Musa x paradisiaca, Musa basjoo, Musa coccinea* and *Musa acuminata* are preferable;
as a plant belonging to *Zingiber, Zingiber officinale;*
as a plant belonging to *Fragaria, Fragaria x ananassa, Fragaria virginiana, Fragaria chiloensis* and *Fragaria vesca;*
as a plant belonging to *Malus, Malus pumila, Malus domestica, Malus baccata, Malus halliana, Malus floribunda* and *Malus prunifolia;*
as a plant belonging to *Prunus, Prunus mume, Prunus avium, Prunus persica, Prunus armeniaca, Prunus dulcis, Prunus salicina* and *Prunus domestica;*
as a plant belonging to *Pyrus, Pyrus communis, Pyrus pyrifolia, Pyrus calleryana* and *Pyrus pyraster;*
as a plant belonging to *Eriobotrya, Eriobotrya japonica;*
as a plant belonging to *Chaenomeles, Chaenomeles sinensis;*
as a plant belonging to *Rubus, Rubus idaeus* and *Rubus fruticosus;*
as a plant belonging to *Rosa, Rosa rugosa;*
as a plant belonging to *Ficus, Ficus carica;*
as a plant belonging to *Vaccinium, Vaccinium corymbosum, Vaccinium angustifolium, Vaccinium myrtillus, Vaccinium vitis-idaea* and *Vaccinium oxycoccos;*
as a plant belonging to *Actinidia, Actinidia chinensis, Actinidia deliciosa, Actinidia arguta, Actinidia rufa* and *Actinidia polygama;*
as a plant belonging to *Diospyros, Diospyros kaki;*
as a plant belonging to *Camellia, Camellia sinensis;*
as a plant belonging to *Cucumis, Cucumis sativus, Cucumis melo, Cucumis anguria* and *Cucumis metulifer;*
as a plant belonging to *Citrullus, Citrullus lanatus;*
as a plant belonging to *Carica, Carica papaya;*
as a plant belonging to *Vasconcellea, Vasconcellea cundinamarcensis;*
as a plant belonging to *Arabidopsis, Arabidopsis thaliana* and *Arabidopsis lyrata;*
as a plant belonging to *Persea, Persea americana;*
as a plant belonging to *Ananas, Ananas comosus;*
as a plant belonging to *Oryza, Oryza sativa;*
as a plant belonging to *Triticum, Triticum aestivum;*
as a plant belonging to *Hordeum, Hordeum vulgare;*
as a plant belonging to *Zea, Zea mays;*
as a plant belonging to *Sorghum, Sorghum bicolor;*
as a plant belonging to *Brachypodium, Brachypodium distachyon;*
as a plant belonging to *Cocos, Cocos nucifera;*
as a plant belonging to *Vanda, Vanda hybridcultivar;*
as a plant belonging to *Iris, Iris x hollandica;*
as a plant belonging to *Ribes, Ribes nigrum;*
as a plant belonging to *Gypsophila, Gypsophila paniculata, Gypsophila elegans;*
as a plant belonging to *Vitis, Vitis vinifera, Vitis labrusca, Vitis aestivalis, Vitis coignetiae* and *Vitis ficifolia;*
as a plant belonging to *Malpighia, Malpighia glabra;*
as a plant belonging to *Passiflora, Passiflora edulis;*
as a plant belonging to *Ricinus, Ricinus communis;*
as a plant belonging to *Populus, Populus trichocarpa;*
as a plant belonging to *Averrhoa, Averrhoa carambola;*
as a plant belonging to *Medicago, Medicago truncatula;*
as a plant belonging to *Lupinus, Lupinus albus;*
as a plant belonging to *Glycine, Glycine max;*
as a plant belonging to *Clitoria, Clitoria ternatea;*
as a plant belonging to *Mangifer, Mangifer aindica;*
as a plant belonging to *Durio, Durio zibethinus, Durio testudinarius, Durio kutejensis, Durio oxleyanus, Durio graveolens, Durio dulcis;*
as a plant belonging to *Citrus, Citrus limon, Citrus sudachi, Citrus sphaerocarpa, Citrus xparadisi, Citrus junos, Citrus aurantifolia, Citrus unshiu* and *Citrus sinensis;*
as a plant belonging to *Aegle, Aegle marmelos;*
as a plant belonging to *Litchi, Litchi chinensis;*
as a plant belonging to *Theobroma, Theobroma cacao;*
as a plant belonging to *Punica, Punica granatum;*
as a plant belonging to *Clarkia,* fairyfans (*Clarkia breweri*) and Redribbons (*Clarkia concinna*);
as a plant belonging to *Psidium, Psidium guajava;*
as a plant belonging to *Actaea, Actaea racemosa;*
as a plant belonging to *Papaver, Papaver somniferum, Papaver orientale* and *Papaver bracteatum;*
as a plant belonging to *Solanum, Solanum lycopersicum;*
as a plant belonging to *Capsicum, Capsicum annuum* and *Capsicum chinense;*
as a plant belonging to *Nicotiana, Nicotiana tabacum, Nicotiana attenuata;*
as a plant belonging to *Petunia, Petunia x hybrida;*
as a plant belonging to *Osmanthus, Osmanthus fragrans, Osmanthus heterophyllus, Osmanthus marginatus, Osmanthus x fortunei* and *Osmanthus insularis;*
as a plant belonging to *Olea, Olea europaea;*
as a plant belonging to *Salvia, Salvia splendens;*
as a plant belonging to *Granduraria, Glandularia x hybrida;*
as a plant belonging to *Rauvolfias, Rauvolfias erpentina;*
as a plant belonging to *Catharanthus, Catharanthus roseus;*
as a plant belonging to *Magnolia, Magnolia figo, Magnolia compressa, Magnolia champaca, Magnolia kobus, Magnolia obovata* and *Magnolia laevifolia;* and
as a plant belonging to *Chamaemelum, Chamaemelum nobile* and *Chamaemelum fuscatum.*

Of these, durian, apple or tomato is more preferable.

Durian AAT comprises the amino acid sequence represented by SEQ ID NO:1. The nucleotide sequence corresponding to the amino acid sequence represented by the SEQ ID NO:1 is represented by SEQ ID NO:2. Apple AAT comprises the amino acid sequence represented by SEQ ID NO:3 or SEQ ID NO:7. Apple AAT comprising the amino acid sequence represented by SEQ ID NO:3 is a wild type; whereas, AAT comprising the amino acid sequence represented by SEQ ID NO:7 is mutant AAT, in which cysteines at the positions 48, 167, 270, 274 and 447 in the wild type AAT are all substituted with alanine and cysteine at the position 150 with arginine, and which has quadruple mutation of A64V, K117Q, V248A and Q363K (see, Japanese Patent Application No. 2017-538070). The nucleotide sequences corresponding to the amino acid sequences represented by SEQ ID NO:3 and SEQ ID NO:7 are represented by SEQ ID NO:4 and SEQ ID NO:8, respectively.

Tomato AAT comprises the amino acid sequence represented by SEQ ID NO:5. Tomato AAT comprising the amino acid sequence represented by SEQ ID NO:5 is tomato (wild species) A2K-type AAT, which is prepared by substituting alanine at the 2nd amino acid of tomato (wild species) wild type AAT, with lysine. The nucleotide sequence corresponding to the amino acid sequence represented by SEQ ID No. 5 is represented by SEQ ID NO:6.

AAT preferably comprises the amino acid sequence represented by SEQ ID NO:1, 3, 5 or 7, and more preferably, the amino acid sequence represented by SEQ ID NO:1, 5 or 7.

As AAT, a protein consisting of an amino acid sequence derived from, for example, the amino acid sequence represented by SEQ ID NO:1, 3, 5 or 7, and preferably the amino acid sequence represented by SEQ ID NO:1, 5 or 7 by deletion, insertion, substitution and/or addition of one or several amino acids, can be used. The protein herein maintains an alcohol acyltransferase activity to catalyze esterification of 3-hydroxyisobutyryl-CoA.

The "several" used herein refers to 1 to 40, preferably 1 to 20, more preferably 1 to 10, and particularly preferably 5 or less. A mutation such as a deletion can be introduced into an amino acid sequence in accordance with a method known in the art such as the Kunkel method or Gapped duplex method by use of a mutation introduction kit using site-directed mutagenesis such as QuikChange™ Site-Directed Mutagenesis Kit (Stratagene), GeneTailor™ Site-Directed Mutagenesis System (Invitrogen) or TaKaRa Site-Directed Mutagenesis System (Mutan-K, Mutan-Super Express Km (Takara Bio Inc.). Alternatively, a whole gene having a sequence containing a mutation such as a deletion can be artificially synthesized.

As AAT, for example, a protein consisting of an amino acid sequence having a sequence identity of 80% or more, preferably 90% or more, more preferably 95% or more, further preferably 99.5% or more, and particularly preferably 99.9% or more with the amino acid sequence represented by SEQ ID NO:1, 3, 5 or 7 and preferably SEQ ID NO:1, 5 or 7, can be used. The protein herein maintains an alcohol acyltransferase activity to catalyze esterification of 3-hydroxyisobutyryl-CoA.

The "sequence identity" used herein is obtained by aligning the two amino acid sequences to be compared so as to match the residues of them as much as possible, counting the number of the residues matched, dividing the count by the total number of residues and expressing the obtained value in percentage. In the alignment, a gap(s) is appropriately inserted as needed in one or both of the two sequences used in comparison. Such alignment can be carried out by use of a program well-known in the art, such as BLAST, FASTA or CLUSTALW. In the case of inserting gaps, the total number of residues is obtained by counting a single gap as one residue. If the total number of residues thus counted differ between the two sequences to be compared, the total number of the longer one is employed in calculation for dividing the count of matched residues to obtain an identity (%).

As AAT, for example, a protein consisting of the amino acid sequence encoded by DNA, which is hybridized with the complementary strand of the nucleotide sequence represented by SEQ ID NO:2, 4, 6 or 8 and preferably SEQ ID NO:2, 6 or 8 under stringent conditions, can be used. The protein herein maintains an alcohol acyltransferase activity to catalyze esterification of 3-hydroxyisobutyryl-CoA.

Examples of the stringent conditions include, but are not limited to, conditions in which hybridization is carried out by placing a DNA-immobilized nylon membrane in a solution containing 6×SSC (1×SSC is prepared by dissolving 8.76 g of sodium chloride, and 4.41 g of sodium citrate in 1 liter of water), 1% SDS, 100 µg/ml salmon sperm DNA, 0.1% bovine serum albumin, 0.1% polyvinylpyrrolidone and 0.1% ficoll, and keeping the membrane at 65° C. for 20 hours with a probe. Those skilled in the art can determine hybridization conditions in consideration of not only the conditions such as a salt concentration of the buffer mentioned above and temperature but also other conditions such as a probe concentration, a probe length and reaction time. As the conditions for the washing to be carried out after hybridization, for example, "2×SSC, 0.1% SDS, 42° C." and "1×SSC, 0.1% SDS, 37° C.", may be mentioned. As more stringent conditions, for example, "1×SSC, 0.1% SDS, 65° C." and "0.5×SSC, 0.1% SDS, 50° C.", can be mentioned.

The detailed procedure of the hybridization method can be referred to, e.g., Molecular Cloning, A Laboratory Manual 2nd ed. (Cold Spring Harbor Laboratory Press (1989)), Current Protocols in Molecular Biology (John Wiley & Sons (1987-1997)).

When AAT is subjected to a reaction, any form of AAT can be used without limitation as long as it exhibits the catalytic activity as mentioned above; more specifically, a biological tissue containing AAT or a processed material thereof can be directly used. Examples of the biological tissue include a whole plant, a plant organelle (for example, fruit, leaf, petal, stem, seed) and a plant tissue (for example, fruit epidermis, pulp). Examples of the processed material of a biological tissue include a crude enzyme solution of AAT extracted from a biological tissue or purified enzyme thereof.

A method for purifying AAT, which is not particularly limited, is preferably as follows. A tissue of a plant as mentioned above having AAT activity is crushed and suspended in a buffer such as tris-HCl buffer or phosphate buffer. To the resultant crude enzyme solution, ordinary purification methods such as (1) fractionation by precipitation, (2) various chromatographic methods, (3) method for removing small molecule substances such as dialysis and ultrafiltration, are applied singly or appropriately in combination.

A preferable aspect of the AAT purification method is as follows. A biological tissue is frozen with, e.g., liquid nitrogen, ground and subjected to extraction with 5-fold volume of tris-HCl buffer containing DTT (dithiothreitol) and glycerol. Subsequently, the resultant crude enzyme extract is subjected to ion exchange chromatography and a portion not adsorbed is recovered to obtain an enzyme extract. As a result that several methods for preparing a crude enzyme extract were checked, it was found out that the crude enzyme extract can be stably and efficiently obtained by the above method while eliminating an influence of polyphenol contained in a plant. An enzyme protein can be efficiency purified from the obtained enzyme extract by using, e.g., ion exchange chromatography and/or gel filtration column.

[Genetically Modified Microorganism Expressing AAT]

As AAT to be subjected to a reaction, an AAT gene is isolated and introduced into a host-vector system ordinarily used, and then, a microorganism can be transformed with the host-vector system and put in use. Examples of the host include bacteria such as *Escherichia coli*, and bacteria belonging to the genus *Rhodococcus, Pseudomonas, Corynebacterium, Bacillus, Streptococcus* and *Streptomyces*; yeasts such as yeasts of the genus *Saccharomyces, Candida, Shizosaccharomyces* and *Pichia*; and filamentous fungi such as fungi belonging to the genus *Aspergillus*. Of these, particularly *Escherichia coli* is preferably used because it is convenient and efficient.

An AAT gene previously known can be isolated by using an ordinary molecular biology technique such as PCR based on genetic information disclosed in a public database. The nucleotide sequence of an AAT gene can be totally synthesized by a routine method. In contrast, an AAT gene whose genetic information is not known can be isolated by estimating the sequence of the gene in accordance with molecular biology technique based on the amino acid sequence of a purified AAT protein, in the same manner as in the AAT gene previously known. Whether AAT, which is already known or newly found, has the catalytic activity of the present invention can be checked by the aforementioned method.

The culture solution obtained by culturing a recombinant microorganism can be directly used, or bacteria cells collected from the culture solution by a method such as centrifugation or a processed material of the bacteria cells can be used. Examples of the processed material include bacteria cells treated with, e.g., acetone and toluene; lyophilized bacteria cells, crushed bacteria cells, a cell-free extract from the crushed bacteria cells, and a crude or purified enzyme extracted from the bacteria cells.

3-Hydroxyisobutyryl-CoA may be synthesized from methacrylyl-CoA within a living microorganism.

Alcohol acyltransferase is reactive to not only 3-hydroxyisobutyryl-CoA but also methacrylyl-CoA and produces a methacrylic ester from methacrylyl-CoA. If alcohol acyltransferase is highly reactive to methacrylyl-CoA, the amount of alcohol acyltransferase, which functions in the reaction of 3-hydroxyisobutyryl-CoA toward a 3-hydroxyisobutyric acid ester, decreases. As a result, the production efficiency of a desired 3-hydroxyisobutyric acid ester decreases.

Accordingly, in order to efficiently produce a 3-hydroxyisobutyric acid ester from 3-hydroxyisobutyryl-CoA, it is preferable to use an alcohol acyltransferase having a higher ratio of activity to methacrylyl-CoA and activity to 3-hydroxyisobutyryl-CoA (activity to 3-hydroxyisobutyryl-CoA/activity to methacryloyl-CoA). As an example of such an alcohol acyltransferase, the alcohol acyltransferase derived from durian can be suitably employed (see Example 4).

A 3-hydroxyisobutyric acid ester and a starting material thereof, i.e., 3-hydroxyisobutyryl-CoA, are low in toxicity because they do not have a highly reactive double bond at the position-alpha, unlike a methacrylic ester and a possible starting material such as methacrylic acid and methacrylyl-CoA. The 3-hydroxyisobutyric acid ester has a high water solubility compared to methacrylic acid. The method for producing a methacrylic ester according to the present invention by using a 3-hydroxyisobutyric acid ester low in toxicity and high in water solubility as a starting material, produces an advantageous effect, particularly, in the reaction system using a microorganism.

In step A, 3-hydroxyisobutyryl CoA and an alcohol or phenol are added in a solvent and dissolved or suspended. Then, AAT is brought into contact with the solution or suspension to react 3-hydroxyisobutyryl CoA with an alcohol or phenol while controlling conditions such as temperature. By the reaction, the 3-hydroxyisobutyryl group of 3-hydroxyisobutyryl CoA is transferred to an alcohol or phenol to produce a 3-hydroxyisobutyric acid ester.

As the solvent, usually, an aqueous solvent such as a buffer is used.

If bacteria cells are used, in order to smoothly facilitate the reaction, osmolality and/or ionic strength may be regulated by an osmo-regulator, or the like. As the osmo-regulator, any water soluble substance may be used as long as it is added for controlling the osmotic pressure of bacterial intracellular fluid to be isotonic or hypotonic; for example, a salt or a sugar, preferably, a salt is used. The salt is preferably a metal salt, more preferably, an alkali metal salt, and more preferably, an alkali metal halide such as sodium chloride and potassium chloride. The sugar is preferably a monosaccharide or an oligosaccharide, and more preferably, a monosaccharide or a disaccharide such as glucose, sucrose and mannitol. The osmo-regulator is preferably added in a concentration of 1 mM or more and particularly preferably added so as to regulate a reaction solution to be isotonic or hypertonic to the intracellular fluid.

For separating the 3-hydroxyisobutyric acid ester produced, an organic solvent can be added in advance and the reaction can be carried out in a two-phase system. As the organic solvent, for example, a linear, branched or cyclic saturated or unsaturated aliphatic hydrocarbon and a saturated or unsaturated aromatic hydrocarbon can be used singly or as a mixture of 2 or more. Examples of the organic solvent include a hydrocarbon solvent (for example, pentane, hexane, cyclohexane, benzene, toluene, xylene), a halogenated hydrocarbon solvent (for example, methylene chloride, chloroform), an ether type solvent (for example, diethyl ether, dipropyl ether, diisopropyl ether, dibutyl ether, tert-butyl methyl ether, dimethoxyethane) and an ester solvent (for example, methyl formate, methyl acetate, ethyl acetate, butyl acetate, methyl propionate). If an organic solvent as mentioned above is added in advance, a 3-hydroxyisobutyric acid ester migrates into an organic phase to efficiently facilitate the reaction.

The molar ratio of 3-hydroxyisobutyryl CoA, an alcohol or phenol and AAT, and concentrations thereof are not particularly limited and can be appropriately controlled. For example, 3-hydroxyisobutyryl CoA, an alcohol or phenol and AAT are preferably present in a ratio of 100 pM to 10 mM:10 μM to 1 M:1 pM to 10 mM. Conditions such as reaction temperature and reaction time are not particularly limited and can be appropriately set. The reaction temperature and reaction time are usually 5 to 80° C. for 20 minutes to 1 week, preferably, 10 to 70° C. for 20 minutes to 120 hours, more preferably 10 to 70° C., for 20 minutes to 60 hours and further preferably, 10 to 70° C. for 20 minutes to 40 hours. The pH of the reaction solution is not particularly limited; for example, falls within the range of pH 4 to 10 and preferably pH 5.0 to 9.0.

[Dehydration Reaction of 3-Hydroxyisobutyric Acid Ester]

In step B, a 3-hydroxyisobutyric acid ester is dehydrated by a conventional chemical method to produce a methacrylic ester.

As the chemical method, for example, the method disclosed in Patent Literature 3 can be employed. More specifically, dehydration can be made by a gas-phase reaction using a solid catalyst such as silica, silica-alumina, zeolite and a solid phosphate under normal pressure at a temperature of 200 to 500° C. Alternatively, dehydration can be made by a liquid phase reaction using, e.g., sulfuric acid and phosphoric acid.

The methacrylic ester produced can be detected and quantified by an ordinary method such as high performance liquid chromatography and LC-MS. The methacrylic ester, which is vaporized and stored in a gaseous phase (head space) in a culture vessel or a reaction vessel, can be detected and quantified by an ordinary method such as gas chromatography.

A methacrylic ester can be isolated from a reaction solution by an operation well known in the art such as filtration, centrifugation, concentration under vacuum, ion exchange or adsorption chromatography, solvent extraction, distillation and crystallization, which are, if necessary, appropriately used in combination. The obtained methacrylic ester can be used as a starting material for acrylic resins or a comonomer for, e.g., paints, adhesives and resin modifiers.

EXAMPLES

Example 1: Measurement of Durian AAT Activity

1. Purification of Durian AAT

Fruit of durian (*Durio zibethinus*) was ground in liquid nitrogen into powder and suspended in a buffer (200 mM Tris-HCl (pH 8.0), 5 mM 2-mercaptoethanol) and filtered with gauze. The filtrate was centrifuged and the supernatant was isolated. To the supernatant, hexane was added and stirred, and then, the mixture was centrifuged and separated into an oil layer and an aqueous layer. The aqueous layer was obtained as a crude enzyme solution. The AAT activity of the crude enzyme solution was measured by the method described later.

To the crude enzyme solution, ammonium sulfate was added. A fraction of an addition concentration of 30% to 60% was dialyzed against a buffer A (20 mM Tris-HCl (pH 8.0), 5 mM 2-mercaptoethanol) (dialysis fraction 1).

The dialysis fraction 1 was supplied to Q-Sepharose column and sufficiently washed with the buffer A. Thereafter, elution was carried out by increasing the concentration of sodium chloride. The eluate was recovered and dialyzed against a buffer B (20 mM Tris-HCl (pH 8.0), 5 mM 2-mercaptoethanol, 30% saturated ammonium sulfate) (dialysis fraction 2).

Subsequently, the dialysis fraction 2 was supplied to Resource PHE column and sufficiently washed with the buffer B. Elution was carried out by decreasing the concentration of ammonium sulfate. The eluate was recovered and dialyzed against the buffer A (dialysis fraction 3).

The dialysis fraction 3 was supplied to MonoQ 10/100 column and sufficiently washed with the buffer A. Then, elution was carried out by increasing the concentration of sodium chloride. The eluate was recovered and dialyzed against a buffer C (50 mM Tris-HCl (pH 8.0), 5 mM 2-mercaptoethanol, 150 mM sodium chloride) (dialysis fraction 4).

Finally, the dialysis fraction 4 was supplied to Superdex 200 column equilibrized with the buffer C. The eluate was recovered and used as a purified enzyme solution. The purified enzyme solution was subjected to SDS-PAGE. As a result, a single band was observed at 53 kDa.

2. Method for Measuring AAT Activity

The AAT activities of the crude enzyme solution, dialysis fractions 1 to 4 and purified enzyme solution were measured by the following method.

First, 100 µl of a reaction solution (100 mM sodium phosphate buffer (pH 7.0), 40 mM n-butanol, 0.50 mM methacrylyl-CoA) was prepared. To the reaction solution, the crude enzyme solution, dialysis fractions 1 to 4 or purified enzyme solution was added and sealed. A reaction was carried out at 30° C. for 30 minutes. After completion of the reaction, 10 mM 2-hexanone (10 µl) was added as an internal reference and extraction was carried out with a solvent, octane (100 µl). A solution (8 µl) centrifugally separated was subjected to gas chromatography (GC) to measure the amount of butyl methacrylate produced by an enzymatic reaction. The amount of the methacrylic ester was calculated based on a calibration curve prepared in accordance with the internal reference method.

Conditions for GC Analysis
  Column: DB-WAX (inner diameter 0.25 mm×60 m, 0.5 µm, Agilent Technologies)
  Column temperature: 100° C. for 5 min, then, the temperature was raised at a rate of 40° C./min, 200° C. for 2 min.
  Carrier gas: helium
  Detection: FID
  Injection temperature: 230° C.
  Detection temperature: 250° C.

The yields and activities of the enzyme compositions in individual purification stages are shown in "Table 1". 195 mU/mg AAT purified with a concentration rate of 2334 fold in its activity was obtained by ammonium sulfate fractionation and column separation repeated four times.

TABLE 1

|  | Amount of protein (mg) | Yield (%) | Activity value (mU) | Specific activity (mU/mg) | Activity ratio |
|---|---|---|---|---|---|
| Crude enzyme solution (Crude extract) | 29000 | 100 | 2500 | 0.0834 | 1.00 |
| Dialysis fraction 1 (Ammonium sulfate fraction) | 14000 | 87.1 | 2149 | 0.153 | 1.80 |
| Dialysis fraction 2 (Q-sepharose) | 912 | 20.4 | 502 | 0.551 | 6.60 |
| Dialysis fraction 3 (Resource PHE) | 4.01 | 5.39 | 133 | 33.2 | 398 |
| Dialysis fraction 4 (MonoQ 10/100) | 0.996 | 2.36 | 58 | 58.3 | 699 |
| Purified enzyme solution (Superdex 200) | 0.107 | 0.85 | 21 | 195 | 2334 |

Example 2: Identification of Durian AAT Gene

Total RNA was extracted from seed coat, loculus and seeds of durian by use of a commercially available kit (PureLink Plant RNA Reagent, Thermo Fisher Scientific). From the total RNA, cDNA was synthesized by a commercially available kit (SMART RACE cDNA Amplification Kit, Takara Bio Inc., or GeneRacer Kit, Thermo Fisher Scientific).

A primer pair was designed based on the nucleotide sequence conserved in AAT derived from a plant and used for amplification of a DNA fragment from cDNA. The amplified fragment (700 bp) obtained was sequenced.

A primer was designed based on the nucleotide sequence of the above amplified fragment, 5'RACE and 3'RACE using cDNA were carried out. The nucleotide sequences of the amplified fragments (about 1.1 kbp and about 1.0 kbp) were determined. In this manner, the durian AAT gene sequence represented by SEQ ID NO:2 was obtained.

Example 3: Preparation of Recombinant *Escherichia coli* Expressing Durian AAT Gene and Purification of Recombinant Durian AAT 1. Preparation of AAT Expression Vector (pET21-NHisMBPTEV-optDzibAAT)

A DNA fragment containing a His-tag sequence, an MBP (Maltose Binding Protein) sequence and a TEV protease cleavage sequence was integrated into vector pET21a (Novagen) to obtain a vector, pET21-NHisMBPTEV.

The codons of durian AAT gene sequence represented by SEQ ID NO:2 were optimized so as to match those of *Escherichia coli*. A codon optimized AAT gene sequence (containing a TEV protease cleavage sequence and a restriction enzyme recognition sequence as addition sequences) represented by SEQ ID NO:9 was synthesized by outsourcing and integrated into the vector pET21-NHisMBPTEV to obtain an expression vector, pET21-NHisMBPTEV-optDzibAAT.

The expression vector, pET21-NHisMBPTEV-optDzibAAT was introduced into *Escherichia coli* NiCo21 (DE3) (New England Biolabs Inc.) to obtain a recombinant, NiCo21 (DE3)/pET21-NHisMBPTEV-optDzibAAT.

2. Purification of Recombinant Durian AAT

An *Escherichia coli* recombinant NiCo21 (DE3)/pET21-NHisMBPTEV-optDzibAAT was inoculated in an ampicillin-containing 2× YT liquid medium (200 mL) and pre-cultured at 37° C. for 16 hours. An aliquot (100 mL) was taken from the culture solution and added to the same medium (20 L) as mentioned above and cultured at 37° C. After the culture was carried out while shaking until the turbidity (OD) reached 1.2, IPTG (final concentration 0.5 mM) was added. Culture was carried out while shaking for further 16 hours by reducing the culture temperature to 20° C. From the resultant culture solution, bacterial cells were centrifugally collected and suspended in a buffer D (20 mM Tris-HCl (pH 8.0), 300 mM NaCl, 10 mM imidazole, 0.2 mM Tris (2-carboxyethyl)phosphine Hydrochloride). While the cell suspension was cooled on ice, the bacterial cells were crushed by an ultrasonic crusher for 30 minutes and centrifuged. The supernatant was obtained as a cell extract.

The cell extract was subjected to an Ni-NTA column and sufficiently washed with the buffer D. Elution was carried out by increasing the concentration of imidazole. A fraction exhibiting absorption of light at 280 nm was recovered and subjected to SDS-PAGE. A band present at the molecular weight matching that of a desired MBP-AAT fusion protein was recovered and dialyzed against the buffer D at 4° C. for 16 hours (dialysis fraction 1).

To the dialysis fraction 1, 500 U of TEV protease (Pro-TEV Plus, Promega KK.) was added. The mixture was allowed to stand still at 4° C. for 48 hours to cleave His tag-MBP. Dialysis fraction 1 was supplied in an Ni-NTA column and the cleaved His tag-MBP was allowed to adsorb. To fractions from the column and containing AAT, a 80% saturated ammonium sulfate solution was added such that the concentration of saturated ammonium sulfate became 25% and the resultant solution was supplied in an amylose column (New England Biolabs Inc.) to obtain a fraction from the column. The fraction was supplied in a TOYOPEARL Butyl-600 column (Tohso Corporation) and sufficiently washed with a buffer E containing 25% saturated ammonium sulfate (20 mM Tris-HCl (pH 7.5), 1 mM EDTA, 1 mM DTT). Thereafter, elution was carried out by reducing the concentration of ammonium sulfate. A fraction exhibiting absorption of light at 280 nm was recovered and subjected to SDS-PAGE. The band present at a molecular weight matching with that of AAT was recovered and dialyzed against the buffer E at 4° C. for 16 hours (dialysis fraction 2).

Finally, the dialysis fraction 3 was supplied in a SP Sepharose column (GE Health Care) and sufficiently washed with the buffer E. Thereafter, elution was carried out by increasing the concentration of sodium chloride. The obtained eluate was recovered as a purified enzyme solution.

By the method described in Example 1, the AAT activities of the cell extract, dialysis fractions 1, 2 and the purified enzyme solution were measured. The yields and activities of the enzyme composition in individual purification stages are shown in "Table 2". Purified AAT (16.4 mU/mg) increased in activity up to 1195 fold was obtained by three column separations.

TABLE 2

|  | Amount of protein (mg) | Yield (%) | Specific activity (U/mg) | Activity ratio |
|---|---|---|---|---|
| Cell extract (cell lysate) | 12146 | 100 | 0.014 | 1 |
| Dialysis fraction 1 (Ni-NTA) | 550 | 106 | 0.33 | 23.6 |
| Dialysis fraction 2 (TOYOPEARL Butyl-600) | 7.46 | 38.6 | 8.65 | 629 |
| Purified enzyme solution (SP Sepharose) | 2.76 | 27.2 | 16.4 | 1195 |

Example 4: Production of Butyl 3-Hydroxyisobutyrate by AAT

A reaction solution 100 µl (100 mM sodium phosphate buffer (pH 7.0), 40 mM n-butanol, 0.5 mM 3-hydroxyisobutyryl-CoA) was prepared. The purified enzyme solution obtained in Example 3 was added to the reaction solution and sealed. A reaction was carried out at 30° C. for 30 minutes. After completion of the reaction, 10 mM 2-hexanone (10 µl) was added as an internal reference and extraction was carried out with a solvent, octane (100 µl). A solution (8 µl) centrifugally separated was subjected to gas chromatography (GC) to measure butyl 3-hydroxyisobutyrate produced by an enzymatic reaction. The amount of the hydroxyisobutyrate ester was calculated based on a calibration curve prepared in accordance with the internal reference method.

GC Analysis Conditions
  Column: DB-WAX (inner diameter 0.25 mm×60 m, 0.5 µm, Agilent Technologies)
  Column temperature: 100° C. for 5 min, then the temperature was raised at a rate of 40° C./min, 240° C. for 2 min.
  Carrier gas: helium
  Detection: FID
  Injection temperature: 300° C.
  Detection temperature: 300° C.

As a purified enzyme, durian AAT (1 µg/ml) was added. After completion of a reaction, the resultant solution was subjected to GC analysis. From the reaction solution to which AAT was added, 0.13 mM butyl 3-hydroxyisobutyrate was detected. The specific activity thereof was 6.1 (U/mg).

The ratio of the activity of durian AAT to 3-hydroxyisobutyryl-CoA and the activity of durian AAT to methacrylyl-CoA (activity to 3-hydroxyisobutyryl-CoA/activity to methacrylyl-CoA) was 37% (6.1/16.4). The value is significantly high compared to the values of apple AAT and tomato AAT (described later). From this, it was made clear that durian AAT has high reactivity to isobutyryl-CoA.

Example 5: Production of Butyl 3-Hydroxyisobutyrate by Plant AATs

1. Recombinant *Escherichia coli* Expressing Apple AAT Gene and Recombinant *Escherichia coli* Expressing Tomato AAT Gene A plasmid pAAT154, which contains a mutant AAT (SEQ ID NO:7) gene in which cysteines at the position 48, 167, 270, 274 and 447 in the wild type apple AAT (SEQ ID NO:3) all are substituted with alanine and cysteine at the position 150 with arginine and which has quadruple mutation of A64V, K117Q, V248A and Q363K, was prepared in accordance with the method disclosed in the literature (Japanese Patent Application No. 2017-538070).

Also, plasmid pAAT032 containing a tomato (wild species) A2K-type AAT (SEQ ID NO:5) gene, which is prepared by substituting the 2nd amino acid (alanine) of tomato (wild species) wild type AAT with lysine, was synthesized by outsourcing (Genscript, hereinafter outsourced to the same company).

Apple AAT expression vector pAAT154 and tomato AAT expression vector pAAT032 were (separately) introduced in *Escherichia coli* JM109 strain to obtain recombinants.

2. Preparation of a Cell Extract Containing AAT

To LB (1% Bacto-tryptone, 0.5% Bacto-yeast extract, 1% NaCl) medium containing ampicillin, each of the *Escherichia coli* recombinants (transformants) was inoculated and the LB medium was subjected to pre-culture performed at 37° C. for 7 hours.

An aliquot (200 µl) of the culture solution was taken and added in 100 ml of the same medium as above (containing 1 mM IPTG). Culture was carried out at 37° C. for 15 hours while shaking.

Bacterial cells were recovered from the culture solution, washed with a 50 mM phosphate-sodium buffer (pH 7.0) and suspended in the same buffer.

The resultant cell suspension was adjusted so as to obtain an OD630 of 20.

The cells were crushed by sonication, centrifuged to remove bacteria cells and membrane fraction, then, filtered by use of Nalgene Rapid-flow Bottle Top Filter (pore size of 0.2 µm, manufactured by Thermo Fisher Scientific) to prepare a cell extract.

3. Concentration of Cell Extract Containing AAT

The obtained cell extract was centrifuged at a centrifugal force of 14,400 g for 30 minutes and the supernatant was isolated. The supernatant was subjected to ultrafiltration membrane Vivaspin filter unit (manufactured by Sartorius) having a molecular weight cut-off of 1,000,000. The fraction from the unit was subjected to ultrafiltration membrane Amicon Ultra filter unit (manufactured by Merck) having a molecular weight cut-off of 30,000 to concentrate up to a 1/10 to 1/20 liquid volume.

4. Measurement of AAT Activity of Cell Extract Containing AAT Concentrated

To 180 µl of a reaction solution containing 0.5 mM 3-hydroxyisobutyryl-CoA and 40 mM n-butanol, 20 µl of the cell extract was added to initiate a reaction for producing butyl 3-hydroxyisobutyrate. The reaction was carried out in a vial of 2 ml in volume. The vial was incubated at 30° C. for 15 to 35 hours to facilitate the reaction. After completion of the reaction, 0.8 ml of ethyl acetate was added to the reaction solution in the vial, stirred and allowed to stand still. Thereafter, the resultant ethyl acetate layer was separated and subjected to GC analysis.

GC Analysis Conditions
  Apparatus: GC-2010 (Shimadzu Corporation)
  Column: DB-1 30 m×0.25 mmID 0.25 µm
  Column flow rate: He 1.0 mL/min
  Temperature raising condition: 50° C., thereafter, raised at a rate of 10° C./min up to 150°, and further at a rate of 20° C./min up to 300° C.
  Detection: FID
  Injection temperature: 220° C.
  Detection temperature: 300° C.
  Split ratio: 1/20
  GC injection volume: 1.0 µL To 900 µl of a reaction solution containing 0.5 mM methacrylyl-CoA and 40 mM n-butanol, 100 µl of the cell extract was added to initiate a reaction for producing butyl methacrylate. The reaction was carried out in a sample bottle (for GC) of 10 ml in volume. The sample bottle was subjected to incubation performed at 30° C. for 1 to 5 hours to facilitate the reaction. After completion of the reaction, 1 ml of acetonitrile was added to the reaction solution in the sample bottle and stirred. Thereafter, the reaction solution was filtered by a syringe filter DISMIC (pore diameter 0.45 µm, manufactured by ADVANTEC) and subjected to HPLC analysis.

HPLC Analysis Conditions:
  Apparatus: Waters 2695
  Column: Shiseido CAPCELL PAK C18 UG120 5 µm
  Mobile phase: 65% MeOH, 0.2% phosphoric acid
  Flow rate: 0.25 ml/min
  Column temperature: 35° C.
  Detection: UV 210 nm
  Injection volume: 10 µL From the reaction solution to which a cell extract containing apple AAT, tomato AAT or durian AAT, butyl 3-hydroxyisobutyrate was detected.

From the yields of butyl 3-hydroxyisobutyrate and butyl methacrylate, the activities of apple AAT and tomato AAT to 3-hydroxyisobutyryl-CoA (3HIBA-CoA) and methacrylyl-CoA (MAA-CoA) were evaluated (see Table 3).

TABLE 3

| Plasmid name | AAT gene encoded | Activity to 3HIBA-CoA (U/L) | Activity to MAA-CoA (U/L) | Activity ratio of 3HIBA-CoA/MAA-CoA (%) |
|---|---|---|---|---|
| pAAT154 | Mutant apple-type AAT | 0.062 | 178.2 | 0.03% |
| pAAT032 | Tomato (wild type) A2K-type AAT | 0.086 | 1.6 | 5.4% |
| pTrc99A | Vacant vector | N.D. | N.D. | — |

N.D. = Not Detected

Sequence Listing Free Text
  SEQ ID NO:1: Amino acid sequence of durian AAT
  SEQ ID NO:2: Nucleotide sequence of durian AAT gene
  SEQ ID NO:3: Amino acid sequence of apple AAT
  SEQ ID NO:4: Codon-optimized apple AAT gene sequence SEQ ID NO:5: Amino acid sequence of tomato A2K-type AAT SEQ ID NO:6: Codon optimized tomato A2K-type AAT gene sequence SEQ ID NO:7: Amino acid sequence of mutant apple AAT SEQ ID NO:8: Codon-optimized mutant apple AAT gene sequence SEQ ID NO:9: Codon-optimized durian AAT gene sequence (containing a TEV protease cleavage sequence and a restriction enzyme recognition sequence as addition sequences)

The invention claimed is:

1. A method for producing a 3-hydroxyisobutyric acid ester, comprising reacting an alcohol or phenol with 3-hydroxyisobutyryl-CoA in the presence of an alcohol acyltransferase to produce a 3-hydroxyisobutyric acid ester, wherein
the alcohol acyltransferase is any one of the following proteins (1) to (3):
(1) a protein comprising the amino acid sequence of SEQ ID NO:1;
(2) a protein comprising an amino acid sequence derived from the amino acid sequence of the SEQ ID NO:1 by deletion, insertion, substitution and/or addition of one or several amino acids, and having an alcohol acyltransferase activity catalyzing esterification of 3-hydroxyisobutyryl-CoA; and
(3) a protein comprising an amino acid sequence having a sequence identity of 80% or more with the amino acid sequence of SEQ ID NO:1 and having an alcohol acyltransferase activity that catalyzes esterification of 3-hydroxyisobutyryl-CoA,
wherein the presence of alcohol acyltransferase is provided by a genetically modified microorganism expressing the alcohol acyltransferase.

2. The method for producing a 3-hydroxyisobutyric acid ester according to claim 1, wherein the 3-hydroxyisobutyryl-CoA is synthesized from methacrylyl-CoA in vivo within the microorganism.

3. The method for producing a 3-hydroxyisobutyric acid ester according to claim 1, wherein the alcohol acyltransferase is (1) a protein comprising the amino acid sequence of SEQ ID NO:1.

4. The method for producing a 3-hydroxyisobutyric acid ester according to claim 1, wherein the alcohol acyltransferase is (2) a protein comprising an amino acid sequence derived from the amino acid sequence of the SEQ ID NO:1 by deletion, insertion, substitution and/or addition of one or several amino acids, and having an alcohol acyltransferase activity catalyzing esterification of 3-hydroxyisobutyryl-CoA.

5. The method for producing a 3-hydroxyisobutyric acid ester according to claim 1, wherein the alcohol acyltransferase is (3) a protein comprising an amino acid sequence having a sequence identity of 80% or more with the amino acid sequence of SEQ ID NO:1 and having an alcohol acyltransferase activity that catalyzes esterification of 3-hydroxyisobutyryl-CoA.

6. A method for producing a methacrylic ester, comprising:
reacting an alcohol with 3-hydroxyisobutyryl-CoA in the presence of alcohol acyltransferase to produce a 3-hydroxyisobutyric acid ester, and
subjecting the 3-hydroxyisobutyric acid ester to a dehydration reaction to produce a methacrylic ester, wherein the alcohol acyltransferase is any one of the following proteins (1) to (3):

(1) a protein comprising the amino acid sequence of SEQ ID NO:1;
(2) a protein comprising an amino acid sequence derived from the amino acid sequence of SEQ ID NO:1 by deletion, insertion, substitution and/or addition of one or several amino acids, and having an alcohol acyltransferase activity catalyzing esterification of 3-hydroxyisobutyryl-CoA; and
(3) a protein comprising an amino acid sequence having a sequence identity of 80% or more with the amino acid sequence of SEQ ID NO:1 and having an alcohol acyltransferase activity that catalyzes esterification of 3-hydroxyisobutyryl-CoA, wherein the presence of alcohol acyltransferase is provided by a genetically modified microorganism expressing the alcohol acyltransferase.

7. The method for producing a methacrylic ester according to claim 6, wherein the alcohol acyltransferase is (1) a protein comprising the amino acid sequence of SEQ ID NO: 1.

8. The method for producing a methacrylic ester according to claim 6, wherein the alcohol acyltransferase is (2) a protein comprising an amino acid sequence derived from the amino acid sequence of SEQ ID NO:1 by deletion, insertion, substitution and/or addition of one or several amino acids, and having an alcohol acyltransferase activity catalyzing esterification of 3-hydroxyisobutyryl-CoA.

9. The method for producing a methacrylic ester according to claim 6, wherein the alcohol acyltransferase is (3) a protein comprising an amino acid sequence having a sequence identity of 80% or more with the amino acid sequence of SEQ ID NO: 1 and having an alcohol acyltransferase activity that catalyzes esterification of 3-hydroxyisobutyryl-CoA.

\* \* \* \* \*